United States Patent
Kober et al.

(10) Patent No.: US 6,288,009 B1
(45) Date of Patent: Sep. 11, 2001

(54) PLANT GROWTH REGULATOR COMPOSITIONS

(75) Inventors: Reiner Kober, Fussgönnheim (DE); David G. Hobbs; Scott W. Gibson, both of Raleigh, NC (US); Kenneth Eugene Fersch, Apex, NC (US); Wilhelm Rademacher; Jörg Botzem, both of Limburgerhof (DE); Markus Frede; Matthias Dernbach, both of Eppelheim (DE); Reimer Göttsche, Baden-Baden (DE); Reinhard Dötzer, Weinheim (DE)

(73) Assignees: BASF Corporation, Mt. Olive, NJ (US); BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/058,641

(22) Filed: Apr. 10, 1998

(51) Int. Cl.$^7$ .................. A01N 63/00; A01N 43/40; C07D 213/06
(52) U.S. Cl. .................. 504/118; 504/130; 546/348
(58) Field of Search .................. 504/130, 118; 546/348

(56) References Cited

U.S. PATENT DOCUMENTS

| | | |
|---|---|---|
| 3,403,304 | 9/1968 | Ross et al. . |
| 3,905,798 | 9/1975 | Zeeh et al. . |
| 4,447,255 | 5/1984 | Schott et al. . |
| 4,634,509 | 1/1987 | Shimizu et al. . |

FOREIGN PATENT DOCUMENTS

| | | |
|---|---|---|
| 0 269 949 A | 6/1988 | (EP) . |
| 0 291 074 A | 11/1988 | (EP) . |
| 0 573 177 | 8/1993 | (EP) . |
| 2-166713 | 2/1990 | (JP) . |
| 02 166713 A | 6/1990 | (JP) . |
| 03 181487 A | 8/1991 | (JP) . |
| 5-265257 | 5/1993 | (JP) . |
| WO 94/09627 | 11/1994 | (WO) . |
| WO 95/02963 | 2/1995 | (WO) . |
| WO 99 09832 A | 3/1999 | (WO) . |

OTHER PUBLICATIONS

H. Strathmann et al., *Better bipolar membranes,* Chemtech, Jun. 1993, pp. 17–24.
International Search Report, PCT/EP99/02188, J. Klaver, mailed Jul. 20, 1999.
Pix Official Handbook, Plant Regulator, BASF Corporation 1996.
Delta Agricultural Digest, 1995, pp. 22–24, Ag Products.
Deciphering PGRs, M. Ray, Cotton Farming, Jun. 1997, pp. 18–20.
Modification of the Branching System of Cotton for Yield Improvement IV. Effect of Growth Regulators on Vegetation Period and Yield, E. R. Khafaga, Angew, Botanik 57, 1983, pp. 257–265.
Effect of Plant Density, Nitrogen Fertilization and Growth Regulators on Cottonseed Yield and Seedling Vigour, Z. M. Sawan et al., J. Agronomy & Plant Science, 154, 1985, pp. 120–128.

*Primary Examiner*—Alan L. Rotman
*Assistant Examiner*—Raymond Covington
(74) *Attorney, Agent, or Firm*—Alston & Bird LLP

(57) ABSTRACT

The invention provides novel mepiquat plant growth regulator compositions which have improved hygroscopicity and corrosion characteristics. The novel mepiquat plant growth regulator compositions of the invention can be readily prepared from technical mepiquat chlorid inter alia by electrochemical ion exchange processes or by quaternization of N-methylpiperidine with dimethylcarbonate as starting material.

19 Claims, No Drawings

PLANT GROWTH REGULATOR COMPOSITIONS

FIELD OF THE INVENTION

The present invention relates to novel plant growth regulator compositions and to the use thereof. More specifically, it relates to compositions comprising mepiquat borate compounds and to methods of plant growth regulation, particularly cotton plant growth regulation.

BACKGROUND OF THE INVENTION

Plant growth regulators (PGRS) affect growth and differentiation of plants. More specifically, various PGRs can, for example, reduce plant height, stimulate seed germination, induce flowering, darken leaf coloring, minimize lodging of cereals, change the rate of plant growth, and modify the timing and efficiency of fruiting.

PGRs are recognized as an essential tool in modern cotton production. Mepiquat (IUPAC name: N,N-dimethylpiperidinium), the first widely accepted PGR for cotton plants, is typically applied to cotton plants in the form of its chloride salt, i.e., mepiquat chloride (the chlorine salt of mepiquat), by foliar application.

The most visible effect of mepiquat chloride PGRs on cotton plants is the reduction of overall plant height, reduction of the distance between nodes, and reduction of plant width. In turn, light penetration to the lower leaves of the plant is enhanced, promoting lower boll retention and development.

A related benefit that is often achieved is an increase in the weight of harvestable cotton bolls. Another highly desirable benefit that is often achieved by using mepiquat chloride PGRs is "earliness" of boll opening. See, for example, Khafaga, Angew. Botanik 57, 257–265 (1983); Sawan et al., J. Agronomy & Plant Science, 154, 120–128 (1985); Ray, Deciphering PGRs, Cotton Farming, June 1997, 18–20; Cotton Production, 1995 Delta Agricultural Digest, 22–24, (published by Argus Agronomics, a division of Argus, Inc.); U.S. Pat. No. 3,905,798, U.S. Pat. No. 4,447,255; Pix Official Handbook.

As discussed in U.S. Pat. No. 3,905,798 to Zeeh et al., all of the known mepiquat salts are hygroscopic solids. Accordingly, dry flowable forms of mepiquat plant growth regulators must be prepared by using various solid carriers such as clays, fertilizers, or the like, or by employing special preparation procedures and packaging that isolate the solids from any humidity in the environment. Further, 95/02963 teaches a process for processing and drying hygroscopic mepiquat chloride for solids formulations and in particular for the production of tablets.

Furthermore, EP-A 573 177 for example discloses an anhydrous process for manufacturing mepiquat chloride, wherein the resulting product must be packed in a water-soluble polyvinylalcohol pouch to protect it against moisture and dissolution as a result of water vapor being taken up.

94/09627 describes the production of water-dispersible granules of mepiquat chloride. Ways are shown of overcoming the hydrgroscopic problems with the aid of selected auxiliaries, e.g., synthetic calcium silicates, binders and mixtures of various sodium sulfonates and/or carboxylates.

In the manufacturing environment, the hygroscopic nature of the mepiquat salts is undesirable for various reasons. In particular, moisture causes the mepiquat chloride salt compositions to disassociate into ions, which in turn tend to have a relatively low pH. The net result is a relatively strong corrosive effect when the moist solids are stored for any substantial period of time. Furthermore higher concentrations of chloride anions in water show strong corrosive effects towards many steel types and metalls. Accordingly, special manufacturing processes and apparatuses are typically employed in order to overcome the corrosive nature of the mepiquat salts.

Further, monoborates of mepiquat, especially monoborates, monoborate chelates or complexes, are used as toners for electrophotography (cf, e.g., JP-A 05/265257; JP-A 02/166713). Aliphatic, open chain quatery ammonium monoborates are described in Electrochim. Acta 39, 18 (1994); Z. Naturforsch. B (Chim. Sci.) 48, 7 (1993); Z. Naturforsch. B (Anorg. Chem. Org. Chem.) 33 B, 20 (1978); J. Nonmetals 2 (2), 103 (1974); JP-A 89/322006; U.S. Pat. No. 3,403,304). These known ammonium monoborates are used as electrolytes, catalytic polymerisation agents, flame retardants or boron-biocides. However no applications are described of these compounds in the agricultural sector.

Although the hygroscopic and corrosive nature of the mepiquat chloride salts is a known problem, no alternative mepiquat compounds have been proposed that are not hygroscopic or corrosive. The search for such compounds is complicated by the requirement that modifications to the compound to decrease its corrosive and hygroscopic properties, must not substantially harm the plant growth regulating properties of the compound. Otherwise, the utility of mepiquat would be eliminated or substantially impaired. In view of such biological activity considerations and further in view of the uniformly hygroscopic nature of all known mepiquat salts, no modified mepiquat compounds which minimize or eliminate these problems while still retaining high biological activity have been proposed.

SUMMARY OF THE INVENTION

The present invention provides novel mepiquat plant growth regulator compositions which have improved levels of corrosivity and hygroscopicity. The novel mepiquat plant growth regulator compositions of the invention can be readily prepared from the commercially available technical mepiquat chloride inter alia by electrochemical ion exchange processes or by quaternization of N-methylpiperidine with dimethylcarbonate as starting material.

The novel mepiquat plant growth regulator compositions of the invention comprise mepiquat borate salts, mepiquat partial borate salts or mixed mepiquat borate salts, including hydrated forms thereof. These mepiquat borate salts, mepiquat particel borate salts or mixed mepiquat borate salts have the formula I $$[DMP]_n{}^{n+}[M_xB_yO_z(A)_v]^{m-}\cdot w\ H_2O \qquad (I)$$

wherein

DMP is N,N-dimethylpiperidinium,

M is a cation of an agriculturally acceptable metal, hydrogen or $NH_4$;

B is boron;

O is oxygen;

A is a chelate or complex-forming moiety associated with at least one boron atom or an agriculturally acceptable cation;

m and n are the same integer in the range of from 1 to 6;

x is an integer or fraction in the range of from 0 to 10;

y is an integer or fraction in the range of from more than 1 to 48;

z is an integer or fraction in the range of from 0 to 48;
v is an integer or fraction in the range of from 0 to 24; and
w is an integer or fraction no the range of from 0 to 24;

The parts of water in formula I represent free or coordinated inner crystalline water or "bonded" water, which is typically expressed as condensed water of boron bonded hydroxy groups for structures of borate.

In the preferred embodiment of the invention A is a molecule from the class of 1-hydroxycarboxylic acids, e.g., lactic acid, mandelic acid or malic acid; mono- or oligohydroxymono-, di- or tricarboxylic acids, e.g., tartaric acid or citric acid; glycols, especially vicinal glycols, e.g., 1,2-propylenglycol, 2,3-butylenglycol; alcohols, e.g., ethanol, pentanol or benzyl alcohol; mono-, di- or tricarboxylic acids, e.g., acetic acid, oxalic acid or benzoic acid; amino alcohols, e.g. ethanolamine or diethanolamine; polyalcohols and sugar and their derivatives such as sugar alcohols, polyhydroxycarboxylic acids, e.g., glycerol, sorbitol, mannitol, glucose and fructose or glucoronic acid; and derivatives of the abovementioned substance classes, e.g., ether or ester derivatives which may form at least one protic-nucleophilic coordination to a boron atom, e.g., ethers or esters with an additional amino, hydroxy or carboxylic acid function.

In one advantageous embodiment of the invention the novel mepiquat plant growth regulator compositions of the invention comprise mepiquat borate salts of the formula II including hydrated forms thereof (= I, with x=0)

$$[DMP]_n^{n+}[B_yO_z(A)_v]^{m-}\cdot w\,(H_2O) \quad (II)$$

wherein:
DMP is N,N-dimethylpiperidinium,
B is boron;
O is oxygen,
A is a chelate or complex-forming moiety associated with at least one boron;
n and m are the same integer in the range of from 1 to 6;
y is an integer or fraction in the range of from more than 1 to 48;
z is an integer or fraction in the range of from 0 to 48;
v is an integer or fraction in the range of from 0 to 24; and
w is an integer or fraction in the range of from 0 to 24.

Especially preferred are compounds of the formula II, wherein y is an integer or fraction in the range of from 2 to 20, very especially preferred in the range of from 2 to 10, particularly preferred in the range of from 3 to 10.

In another advantageous embodiment of the invention, the mepiquat borate salts or partial borate salts set forth above, can be mixed, i.e., complexed, with other agriculturally acceptable salts, preferably borate salts. The complexed or mixed salt compositions of the invention have the overall formula III (= I, with x≠0):

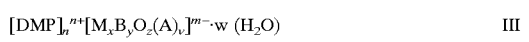

$$[DMP]_n^{n+}[M_xB_yO_z(A)_v]^{m-}\cdot w\,(H_2O) \quad III$$

wherein:
DMP is N,N-dimethylpiperidinium;
M is a cation of an agriculturally acceptable metal, like sodium, potassium, magnesium, calcium, zink, manganese or copper, hydrogen or $NH_4$;
B is boron;
O is oxygen;
A is a chelate or complex-forming moiety associated with at least one boron atom or an agriculturally acceptable cation;
n and m are the same integer in the range of from 1 to 6;
x is an integer or fraction in the range of from more than 0 to 10,
y is an integer or fraction in the range of from more than 1 to 48,
z is an integer or fraction in the range of from 0 to 48,
v is an integer or fraction in the range of from 0 to 24, and
w is an integer or fraction in the range of from 0 to 24;

Especially preferred are compounds of the formula III wherein y is an integer or fraction in the range of from 2 to 20, very especially preferred in the range of from 2 to 10, particularly preferred in the range of from 3 to 10.

In another advantageous embodiment of the invention the novel mepiquat plant growth regulator compositions comprise mepiquat borate salts of the formula I, preferably mepiquat borate salts of the formula II, including hydrated forms thereof, wherein
y is an integer or fraction in the range of from 3 to 7;
z is an integer or fraction in the range of from 6 to 10;
v is zero;
w is an integer or fraction in the range of from 2 to 10;

Especially preferred are compositions comprising compounds of the formula II, wherein
y is an integer or fraction in the range of from 3 to 5;
z is an integer or fraction in the range of from 6 to 8;
v is zero;
w is an integer or fraction in the range of from 2 to 8;

Very especially preferred are compositions comprising compounds of the formula II, wherein
y is five;
z is eight;
v is zero;
w is an integer or fraction in the range of from 2 to 3.

The mepiquat borate, partial borate and mixed borate salts of the invention have improved levels of corrosivity and hygroscopicity. They are biologically active compositions having plant growth regulating properties comparable or superior to mepiquat chloride. The novel mepiquat borates can readily be prepared according to another aspect of the invention by converting salts such as mepiquat halides, carbonates, bicarbonates, sulfates, bisulfates, mono-$C_1$–$C_4$-alkylsulfates or formiates, especially mepiquat halides, sulfates, monomethylsulfate and formiates, preferably mepiquat chloride into basic mepiquat salts such as mepiquat hydroxide by novel electrochemical processes. The abovementioned, basic mepiquat salt is then reacted with boric acid to form the new salts of the mepiquat borate type, corresponding to the formula II and with regard to the compounds of formula III, the abovementioned basic mepiquat salt is reacted with boric acid and other compounds. The conversion of the abovementioned mepiquat salts to mepiquat hydroxide can be conveniently conducted according to yet another aspect of the invention using any of various ion exchange processes. Preferably, mepiquat salts such as mepiquat halides, carbonates, bicarbonates, sulfates, bisulfates, mono-$C_1$–$C_4$-alkylsulfates or formiates, especially mepiquat halides, sulfates, monomethylsulfate and formiates, preferably mepiquat chloride are converted to mepiquat hydroxide using electrochemical ion exchange processes and apparatus.

Furthermore, the novel mepiquat borates can readily be prepared according to another aspect of the invention by converting mepiquat chloride directly into mepiquat borates by a novel electrochemical process which will be described later on in detail.

The mepiquat borates can also be prepared using mepiquat hydroxide, bicarbonate or carbonate as educts by classic inorganic reactions. Preferentially the abovementioned novel carbonates or bicarbonates can be obtained by quaternization of N-methylpyridine and/or piperidine with dimethylcarbonate in the heat, preferentially under pressure and by using methanol and/or water as solvents. Mepiquat carbonate and/or bicarbonate are then reacted with boric acid and/or corresponding borate salts. As an option, basic salts of agriculturally acceptable metals, which were mentioned for formula III, especially their basic metal hydroxides or carbonates can be used.

In all the abovementioned cases a chelate or complex forming moiety A can be added to get compositions comprising compounds of the formula I to III with v≠zero.

In preferred embodiments of the invention, the compositions comprising the mepiquat borate, partial borate, and mixed borate salts (collectively referred to hereinafter as "mepiquat borates") are substantially free of chlorine or other halide ions.

Typical values of halide traces and halide contaminations are in a range of from 0 to 1 wt. %, preferentially of from 0 to 0.5 wt. % based on mepiquat borates (calc. dry).

It is also preferred for the mepiquat borates of the invention to have a pH in aqueous solution between about 5 and about 9 preferably approximately neutral.

Preferred mepiquat borates of the invention include sufficient boron for the ratio of elemental boron to mepiquat cation to be between about 1:2 and about 20:1, more preferably between about 2:1 and about 20:1, especially preferably between about 2:1 and about 10:1, in particular between about 3:1 and about 10:1. At least in some cases, it is believed that the borate anions or moieties, complexed or associated with the mepiquat cation, are capable of potentiating or otherwise enhancing the plant growth regulating properties of mepiquat, as disclosed in detail in U.S. Patent application entitled "POTENTIATED MEPIQUAT PLANT GROWTH REGULATOR COMPOSITIONS" filed Aug. 25, 1997 by Kenneth E. Fersch, Scott W. Gibson, and David G. Hobbs, U.S. application Ser. No. 08/920,196 which is hereby incorporated by reference.

The novel mepiquat plant growth regulator compositions of the invention are particularly desirable because of their non-hygroscopic and non-corrosive properties as discussed previously. In addition, borate fertilizers in the form of simple borate salts such as SOLUBOR® (U.S. Borax Company) ($Na_2B_8O_{13} \cdot 4 H_2O$) have long been applied to plants such as cotton.

Boron is also a component of complex fertilizer mixtures or micronutrient preparations such as Basfoliar™ or Nutribor™ (BASF AG). Accordingly, preferred mepiquat borates of the invention introduce no new chemical moieties into the environment or into a crop such as cotton. Indeed, the quantity of mepiquat cation applied to crops such as cotton by preferred compositions of the invention, is comparable to or generally the same as applied by conventional mepiquat chloride PGR formulations, while the quantity of boron applied to crops is below the quantity applied by conventional boron fertilizers and above quantities applied by boron micronutrient components of other fertilizers.

DETAILED DESCRIPTION OF THE PREFERRED EMBODIMENTS

The mepiquat borate compositions of the invention, in their various forms, can be generally referred to as "salts", "coordination compounds" or "complexes". Similarly, the cationic and anionic species thereof can be referred to as "ions" or "complex ions". As is apparent to those skilled in the art, the theoretical differences between a "compound", a "coordination compound", a "complex", and a "salt", are generally understood as being a matter of degree, only; and similarly, the theoretical difference, if any, between an "ion" and a "complex ion" is generally understood as being a matter of degree. This is particularly true in the case of inorganic compositions and complexes based boron-oxygen containing anionic moieties. Accordingly, the term "salt" is used herein to include "salts", "coordination compounds" and "complexes"; and the terms "ion", "cation", and "anion" are used herein to include "ions" and "complex ions". The term "agriculturally acceptable" is used herein to include agricultural, industrial and residential uses which are compatible with plants.

The term "mepiquat borate salt" as used herein, is intended to include salts, coordination compounds, and complexes, of mepiquat (N,N-dimethylpiperidinium) cations with borate anions. The term "mepiquat partial borate salt" as used herein is intended to include coordination compounds, complexes and salts, of mepiquat cations with mixed anionic species including both borate anions and at least one other type of anion which does not contain boron. The term "mixed mepiquat borate salt" as used herein, is intended to include coordination compounds, complexes, and salts, of mixed cationic species including both mepiquat cations and at least one other type of cation different from the mepiquat cations, with borate anions alone, or with mixed anionic species including both borate anions and at least one other type of anion which does not contain boron.

The term "borate" as used herein is intended to include hydrated and anhydrous anionic species based on boron-oxygen compounds, in various forms including chain and ring structures, including oligomorphic and polymorphic forms thereof, e.g., double rings.

As is generally known to those skilled in the art, the particular form or structure of a borate anion or polyanion, can readily change depending upon the chemical environment of the anionic species. In particular, the structures of many borate anions are known to vary under different conditions of pH and/or depending on whether the species is present as a solid, or in aqueous solution.

In particular, borate anions in aqueous solution at pH's in the range of 7–9 tend to be present in the form of rings and double rings. Boron NMR studies show that, depending on the concentration, the abovementioned borate anions are especially equilibrium mixtures of mono-, tri- and pentaborate structures (see therefore C. G. Salentine, Inorg. Chem., 22, 3920 (1983).

On the other hand, at pH's below about 6, the borate anions tend to be present in the form of boric acid or as chains having the formula $[BO_2]_q^-$, in which q is typically greater than 1. This happens especially in the heat, for example under the conditions of spraydrying and of condensations and removal of water. However, under usual spraydrying conditions (inlet temperature of from 50 to 200° C., especially of from 80 to 150° C.) tri- and pentaborate anionic structures are mainly obtained.

Moreover, the various anionic borate species typically hydrate, i.e., react and/or complex with water, rapidly and lose their original structure in aqueous solution with the result that the anionic structure in aqueous solution for a particular borate may not be the same as the anionic structure in crystalline or amorphous non-aqueous form since less complex anions can readily combine during a crystallization process.

In a like manner, various polyols and α-hydroxy carboxylic acids, and also various polyamines, are known to form very stable complexes (including chelates), exceedingly rapidly, with borates in aqueous and nonaqueous solutions. Preferably used as complexing/chelating agents are for example the following compounds A.

In detail according to formula I A, means a molecule from the class of 1-hydroxycarboxylic acids, e.g., lactic acid, mandelic acid or malic acid; mono- or oligohydroxymono-, di- or tricarboxylic acids, e.g., tartaric acid or citric acid; glycols, especially vicinal glycoles, e.g., 1,2-propylenglycol, 2,3-butylenglycol; alcohols, e.g., ethanol, pentanol or benzyl alcohol; mono-, di- or tricarboxylic acids, e.g., acetic acid, oxalic acid or benzoic acid; amino alcohols, e.g. ethanolamine or diethanolamine; polyalcohols and sugar and their derivatives such as sugar alcohols, polyhydroxycarboxylic acids, e.g., glycerol, sorbitol, mannitol, glucose and fructose or glucoronic acid; and derivatives of the abovementioned substance classes, e.g., ether or ester derivatives which may form at least one protic-nucleophilic coordination to a boron atom, e.g., ethers or esters with an additional amino, hydroxy or carboxylic acid function.

Furthermore, the term "borate" as used herein, is intended to also include hydrates, polyol complexes, carboxylic acid complexes and amine complexes which are readily derived from borates and hydrated borates. Borate chemistry is discussed in greater detail in various texts known to the skilled artisan including Cotton and Wilkinson, "Advanced Inorganic Chemistry, A Comprehensive Text", Section 8–5, pages 229–233 (Third Edition, 1972); and Hollemann-Wiberg, "Lehrbuch der Anorg. Chemie", 81–90., Aufl., page 631 et seq., "Boron, Metallo-Boron compounds and Boranes", Intersciences Publishers, John Wiley and Sons, 1964 and Wolfgang Kliegel, "Bor in Biologie, Medizin and Pharmazie", Springer Verlag, 1980 - which are incorporated by reference herein.

The compounds I to III of the present invention comprise at least one boron-oxygen-boron fragment as structural element.

The mepiquat borates of the invention can be readily prepared from known mepiquat salts including halides and the like, which in turn can be prepared according to known processes disclosed, for example, in U.S. Pat. No. 3,905,798 to Zeeh et al., which is incorporated herein by reference. Advantageously, the mepiquat borates of the invention are prepared by converting a readily available mepiquat salt, preferably mepiquat chloride, into a basic mepiquat salt such as mepiquat hydroxide and thereafter neutralizing the basic mepiquat salt with boric acid and optionally blending with borates of agriculturally useful salts, like sodium, potassium, ammonium, calcium, magnesium or zinc in order to form the new compounds of formula I.

Furthermore basic salts of the abovementioned agriculturally useful cations, for example oxides, hydroxides, carbonates or hydrogencarbonates of sodium, potassium, calcium, magnesium, zinc or ammonium, can be used in combinations with boric acid or other borate salts.

The conversion of mepiquat salts, e.g., mepiquat halides, carbonates, bicarbonates, sulfates, bisulfates, mono-$C_1$–$C_4$-alkylsulfates or formiates, especially mepiquat halides, sulfates, monomethylsulfate and formiates, preferably mepiquat chloride, to mepiquat hydroxide can be conveniently conducted according to the invention using any of various chemical or electrochemical ion exchange processes, including ion exchange processes using various ion exchange resins, and by electrochemical ion exchange processes. Preferably, mepiquat chloride is converted to mepiquat hydroxide using electrochemical processes and apparatus.

Currently, electrochemical processes employing microporous membrane separators, are preferred processes for the preparation of mepiquat hydroxide. Such electrochemical processes can be conducted in various ways using various known apparatus. For example, bipolar electrodialysis processes can be carried out by method similar to those described in H. Stratmann et al., Chemtech (6) (1993) pages 17–24, which is hereby incorporated by reference.

According to this process, a bipolar electrodialysis cell is fitted with an alternating arrangement of a plurality of bipolar membranes and a plurality of anion exchange membranes. The alternating arrangement of the two membrane types gives rise to a plurality of "n" acid and "n" base zones in which "n" can range from 1 to about 300. The membranes are supported by sealing spacers spaced about 0.05 to about 3 mm apart.

The bipolar electrodialysis process can be conducted in either a basic mode (employing a basic solution including, e.g., sodium hydroxide) or in an acidic mode (employing an acidic solution including, e.g., sulfuric acid). In the basic mode, nickel anodes and steel cathodes are preferred. In the acidic mode preference is given to DSA (dimensionally stable anodes, known from chlorine-alkali-electrolysis, i.e. titanium metal mesh anodes with various mixed oxides, e.g. the transition metals Ir, Ru, Rh, etc.) or Pt anodes and steel or Pt cathodes. The current densities used are in the range between 1 and 14 $A/dm^2$, especially between 4 and 10 $A/dm^2$.

The process is started by pumping a dilute, e.g., 1 to 60 wt. %, preferably 5 to 30 wt. % strength mepiquat salt solution, especially mepiquat halide solution, preferably mepiquat chloride solution through the set of base zones. At the same time, dilute acid (e.g., 0.5 wt. % strength hydrochloric acid) is pumped through the acid zones. When an electric field is applied, chloride ions migrate across the anion exchange membrane, in accordance with the direction of the field, from the base compartments to the acid compartments. At the same time water is dissociated in the bipolar membranes into $H^+$ (acid compartments) and $OH^-$ (base compartments). The pH in the acid loop can be kept acidic or neutral or basic by adding a base. Preferably the acid loop is kept acidic. The bipolar electrodialysis treatment results in a 1 to 60 wt. %, preferably 5 to 30 wt. % strength mepiquat hydroxide solution which is largely chloride-free.

It is especially advantageous when the borates of formula I are synthesized directly without the isolation of the mepiquat hydroxide stage. In doing so the base loop yield of the bipolar electrodialysis arrangement described above is treated during the electrochemical reaction with appropriate quantities of boric acid (crystalline or concentrated boric acid solution), boron containing oxides, and optionally in the presence of agriculturally useful metal hydroxides, metal oxides, metal carbonates, metal bicarbonates, ammonium hydroxide, ammonium carbonate or ammonium bicarbonate or mixtures thereof, so that the compounds of formula I are formed directly. For this purpose an aqueous solution of mepiquat halide, especially mepiquat chloride, having a concentration of 1 to 60 wt. %, especially having a concentration of 5 to 30 wt. %, is charged into the base loop of the bipolar electrodialysis system. A dilute solution (about 0.5 wt. %) of an acid, base or alternatively of a mineral salt, especially hydrogen chloride, sulfuric acid, sodium hydroxide, potassium hydroxide, sodium chloride or potassium chloride, preferably hydrogen chloride or sodium chloride, are charged into the acid loop so that there is adequate initial conductivity. By applying an electric current to the electrodes the chloride ions migrate in accordance with the electric field selectively through the anion exchange membrane into the acid loop, while multivalent anions and cations are held back. At the same time, likewise due to the influence of the electric field, water dissociates in the bipolar membranes into $H^+$ (acid loop) and $OH^-$ (base loop). The liberated hydroxide ions deprotonate the boric acid so that the compounds of formula I are formed directly.

In this process the pH in the acid loop is maintained in the range of 1 to 14, preferebly in the range of 6 to 9, by addition of base. All materials known from the literature can be used for the electrodes. The current densities lie in the range of 1 to 14 $A/dm^2$, preferably between 4 and 10 $A/dm^2$, and especially between 4 and 6 $A/dm^2$.

The concentration of the salts formed in the acid loop usually lies in the range of 1 to 35 wt. %, preferably in the range of 5 to 15 wt. %. The reaction is carried out at 10 to 60° C., preferably at 30 to 50° C. The mepiquat borate salts obtain at most 1 wt. %, and preferably 0.5 wt. % chloride, based on mepiquat borate salt (calc. dry).

An alternative electrochemical process for synthesizing mepiquat hydroxide from the corresponding salt, especially chloride can generally be carried out employing the ion exchange electrolysis process as generally described in GB-A 1066930 (Monsanto). According to this process, a conventional plate/frame electrolytic cell is converted into a bipartite cell by a cation exchange membrane (for example a Nafiono® cation exchange membrane) being placed between the anode and the cathode. The preferred anode material used preferably comprises DSA electrodes and the preferred cathode material used is alloy steel (RA4) or nickel.

The anolyte pumping circuit is supplied with a 5–60 wt. % strength aqueous mepiquat chloride solution. The catholyte pumping circuit is charged with, for example, a 0.5–1 wt. % strength mepiquat hydroxide solution.

The electrolytic process causes selective transfer of mepiquat cations across the cation exchange membrane in the direction of the catholyte, where simultaneous cathodic electrolysis of water generates hydrogen and $OH^-$ ions. The latter, together with the mepiquat cation transferred from the anolyte, form the desired mepiquat hydroxide. The anode reaction takes the form of electrolytic oxidation of chloride ions to elemental chlorine which is continuously removed by continuous scrubbing of the anolyte.

Furthermore the mepiquat borates of the invention can be readily prepared from mepiquat carbonates and hydrocarbonates, which in term can be prepared by quaternazing N-methyl-piperidine with dimethylcarbonate. The mepiquat carbonates and bicarbonates can be used directly—without forming the mepiquat hydroxide—to from the mepiquat borates.

The novel mepiquat borate salts, partial borate salts, and mixed borate salts, are then prepared in accordance with the invention by reacting the basic mepiquat salt (e.g. mepiquat hydroxide, mepiquat carbonate, mepiquat bicarbonate) with boric acid or boric oxide, or with an agriculturally acceptable borate salt and/or a chelating reactant (see the definition for A). Such borate salts include any of various known borate salts including, sodium borate, sodium metaborate, sodium triborate, sodium pentaborate, polyborates, borax, borax decahydrate, borax pentahydrate, disodium octaborate tetrahydrate (commercially available as SOLUBOR® from U.S. Borax, Valencia, Calif.) and the like. The quantity of boric acid or borate salt is selected to provide the desired ratio of elemental boron to mepiquat cation in the final mepiquat borate. Preferably, the mepiquat borates of the invention comprise a weight ratio of mepiquat to boron (calculated based on elemental boron and the mepiquat cation) of at least about 2:1 to 1:20, preferably at least about 1:3 to 1:10. On the other hand, the quantity of elemental boron can be significantly greater than that of the mepiquat cation, and can range up to 1:50 or higher. It is also possible to blend the compounds of the formula II with additional boron sources, like Solubor® or Borax, or with mixtures of boric acid and basic salts of agriculturally acceptable metals, for example oxides, hydroxides, carbonates or bicarbonates of sodium, potassium, calcium or magnesium, to obtain the compounds of the formula III.

Currently preferred mepiquat borates have a boron to mepiquat ratio of between about 2:1 and about 10:1 (calculated based on elemental boron and the mepiquat cation).

The boron to mepiquat ratio is controlled by incorporating non-borate anionic reactants or borate-complexing compounds during the reaction of the basic mepiquat salt with boric acid, or with a borate salt; or by including excess borate anionic materials in the composition either as neutralized boric acid, or directly in the form of an agriculturally acceptable borate salt. Suitable chelating agents or borate-complexing compounds include polyols, particularly lower alkyl glycols and sugars; α-hydroxy carboxylic acids such as lactic acid and mandelic acid; 2,3-dihydroxycarboxylic acids such as tartaric acid or acids like anthranilic aicd, various polyamines such as EDTA, and the like.

Advantageously, the compositions comprising mepiquat borate, partial borate, and mixed borate salts (collectively referred to hereinafter as "omepiquat borates") are substantially free of chlorine or other halide ions, as indicated by a chloride or other halogen content of from 0 to 1 wt. %, especially 0 to 0.5 wt. % compared with the compounds of formula (I). For example borates obtained by the carbonate path contain about 1 ppm or less halogen.

In general when recrystallised and purified in water the borates are substantially free of chloride.

It is also preferred for the mepiquat borates of the invention to have a pH in aqueous solution that is approximately neutral, i.e., between about 5 and about 9.

The mepiquat borate plant growth regulator formulations of the invention are applied to above ground portions of plants, i.e., by foliar application to control plant growth. Plants that can be treated by the compositions or formulations of the invention include any of the plants disclosed in the aforementioned U.S. Pat. No. 3,905,798 to Zeeh et al., and other plants that are conventionally treated with known mepiquat compositions, including wheat, barley and other small grains, grapes, poinsettias and other ornamentals and particularly cotton. Such foliar application can be carried out by various conventional methods and apparatus as are well known in the art including spraying, atomizing, dusting, boom and hand application, hydraulic nozzle, electrostatic atomizers, spreaders, and the like. If desired the product may be applied to using aircraft or helicopters equipped with hydraulic or granular application systems. Desirably, the formulations of the invention are applied in the form of an aqueous solution.

The compositions or formulations of the invention can be applied to cotton and other plants in a single application, but are preferably applied in multiple applications distributed throughout the growing season, wherein the timing of application and the concentration of the active ingredients are varied depending on factors including the species and variety of the plant; the development stage of the plant and the season of the year; the application locality and site; climatic conditions, such as temperature, amount of precipitation, and also length of day and intensity of light; and soil properties, including fertilization. It is currently believed that the compositions or formulations of the invention are best applied in the case of cotton plants at an application rate, calculated based on mepiquat cation, at a rate of from about 1 g/ha to about 100 g/ha, for each application. It is also currently believed that the compositions or formulations of the invention are best applied in the case of cotton plants in accordance with the same considerations as are used in connection with PIX® plant growth regulator compositions, as discussed in for example, PIX® *Plant Regulator, Official Handbook*, 1996, BASF Corporation, Research Triangle Park, N.C., which is incorporated herein by reference.

As with conventional mepiquat, the mepiquat borates of the invention function to inhibit the vegetative growth of plants, which is expressed in particular in a reduction in longitudinal growth. Hence the treated plants exhibit a dwarfed growth; and in most cases, a darker leaf coloration can also be observed. Among other effects, this also makes possible completely mechanized harvesting of this important crop plant. Because of the small relatively leaf and plant mass after treatment, attack by various diseases (such as fungus) can be decreased as well. The inhibition of vegetative growth also makes it possible to space the individual plants more closely, making a higher yield for the acreage possible.

At least in some cases, it is believed that the borate anions or moieties, complexed or associated with the mepiquat cation, are capable of potentiating or otherwise enhancing the plant growth regulating properties of mepiquat. The terms "potentiate" and "potentiated", are used herein, to include both quantitative improvements, and qualitative improvements such as one or more different plant growth affects or properties, that are not enhanced as compared to conventional mepiquat chloride, applied alone, particularly on cotton plants. Thus, in some instances, the compositions of the invention are believed capable of providing increased yields of cotton lint, more vigorous, yet controlled, cotton plant development, and/or shortening of the time required for opening of the cotton boll by one day to several days or longer, depending on the particular growing season, location and weather conditions, and appropriate management of the cotton crop.

The mepiquat borate compositions or formulations of the invention can be supplied for agricultural use in various forms, including package, i.e., concentrated, and tank mix, i.e., ready to use, forms, and also in various concentrations and different physical forms. The mepiquat borate compositions or formulations of the invention can be directly supplied in dry granule, tablet, or powder form because of the non-hygroscopic nature of the compositions. However, they can also be supplied as a liquid concentrate or full strength liquid.

Advantageously, in the form supplied for full strength or for diluted agricultural use, the compositions of the invention are included as an active ingredient in an amount ranging from about 0.01 to about 40 wt. %, calculated based on the weight of mepiquat cation.

Mepiquat borak concentrates made by the different processes for preparation, may be used directly as ready mixes for agricultural uses.

Furthermore the mepiquat borate concentrates can be dried under vacuum by the removal of water or spraydried to give water soluble powders or granules.

If desired, the compositions or formulations can also be provided in the form of a liquid slurry or suspension in which all or a portion of the active ingredient is dissolved or suspended in the liquid.

Slurries or suspension concentrates are often preferred because they contain higher amounts of active ingredient and reduce the volume of packaging.

Preferably the composition is supplied to the consumer for agricultural use in the form of a concentrate in a sealed package. Such packages include glass and plastic bottles and bottle-like containers, carton containers, pouch containers formed of various film, foil, and/or paper materials or laminates thereof, and like containers as will be apparent. In such cases, the concentrate formulation is diluted by the user according to label instructions prior to use thereof, so that the active ingredients are applied at specified rates, discussed in detail below. Typically, a concentrate formulation is diluted in an amount ranging from about 2:1 to about 800:1 (diluent to concentrate).

In typical concentrate formulations, and in the form for application to plants, the formulation will also include one or more agriculturally acceptable diluents as are known in the art, including, in the case of liquid formulations, water, dimethyl sulfoxide, n-methylpyrrolidone, ketones, like cyclohexanone, aromatic and aliphatic hydrocarbon oils, vegetable oils and modified vegetable oils such as esterified vegetable oils, alcohols such as isopropyl and ethyl alcohol, polyols such as ethylene or propylene glycols, esters, and the like.

However some of these mentioned alcohols and polyoles can react in the solution with the borate anions as chelating agents.

In addition, the liquid formulation can also include thickening agents, e.g. xanthane like Kelzan S (Kelco/Monsanto Performance Materials company), natural based agents like guar gum, locust bean gum or alginate like sodium alginate, suspension concentrates of minerals like bentonites or hectorites, technical polymers like polymers or co-polymers of acrylic acid, sodium acrylate or acrylamide monomere or sugar derivatives like carboxy-methyl-cellulose (CMC) or methyl-cellulose and/or further derivatives, technical salts or blends of these compounds. They are used in the range of from 0 to 10 wt %. Especially xanthanes are used, preferably in the range of from 0 to 1 wt. %.

In the case of solid formulations, various clays, binders, and fillers, such as diatomaceous earth, attapulgite, and the like, fertilizers such as ammonium sulfate, ammonium nitrate and urea, solid polyols such as sorbitol, manitol and other sugars, and other solid carriers such as salt, dirt, wood-based or other cellulosic particulate materials, and the like. Various other preferred agriculturally acceptable carriers are disclosed in the aforementioned U.S. Pat. No. 4,447, 255 issued May 8, 1984 to Schott et al. and U.S. Pat. No. 3,905,798, issued Sep. 16, 1975 to Zeeh et al.

In addition, the formulations of the present invention can also include other active ingredients like herbicides, fungicides, insecticides or other PGRs or adjuvants commonly employed in the art, including penetrants, surfactants, crop oils, drift control agents, defoaming agents, preservatives, wetting agents, adherents, antimicrobial agents, and the like, including mixtures thereof, as are also well known in the art and disclosed, for example in the aforementioned U.S. Pat. No. 4,447,255 and U.S. Pat. No. 3,905,798.

Especially ionic or nonionic surfactants, dispergent agents and surfactants can be used in oder to enhance the efficacy of the novel borates.

The following auxiliary agents, e.g., from the following families of materials come into consideration as surfactants, wetting agents and dispersants:

Anionic Surfactants and Dispersants:
Soaps (alkali metal/alkaline earth/ammonium salts of fatty acids) e.g. potassium stearate; alkyl sulfates; alkyl ether sulfates, e.g. sulfated hexa-, hepta- and octadecanols and fatty alcohol glycol ethers; alkyl/isoalkyl sulfonates; alkali metal, alkaline earth and ammonium salts of arylsulfonic acids and alkylbenzenesulfonic acids, such as e.g. ligninsulfonic, phenolsulfonic acids, naphthalenesulfonic and dibutylnaphthalenesulfonic acids or sodium dodecylbenzenesulfonates; alkylnaphthalenesulfonates; methyl alkylsulfonates; acyl glutamates; alkyl succinoylsulfonates; alkyl mono/diphosphates; sarcosinates e.g. sodium lauroylsarcosinate; taurates; additionally, condensation products of sulfonated naphthalene and its derivatives with formaldehyde, condensation products of naphthalenesulfonic acids, phenols and/or phenolsulfonic acids and their salts with formaldehyde and/or urea; protein hydrolysates and especially as dispersants: lignosulfite spent liquor and methylcellulose.

Cationic Surfactants:
Alkyltrimethylammonium halides/alkyl sulfates; alkylpyridinium halides; dialkyldimethylammonium halides/alkyl sulfates;

Nonionic Surfactants:
Poly(ethylene glycol) esters of fatty acids such as lauryl alcohol.
Poly(ethylene glycol) ether acetate; alkyl poly(ethylene glycol) or poly(propylene glycol) ethers, of isotridecyl alcohol for instance, and fatty alcohol-poly(ethylene glycol) ethers; alkylaryl alcohol-poly(ethylene glycol) ethers such as octylphenylpoly(ethylene glycol) ether; alkoxylated animal/vegetable fats and oils e.g. corn oil ethoxylates, castor oil ethoxylates, tallow ethoxylates; glycol esters e.g. glycerol monostearate; fatty alcohol alkoxylates and oxoalcohol alkoxylates; fatty acid alkoxylates e.g. oleic acid ethoxylates; alkylphenyl alkoxylates e.g. ethoxylated isooctyl-, octyl- or nonylphenol, tributylphenol-poly (ethylene glycol) ethers; fatty amine alkoxylates; fatty acid amide alkoxylates; saccharide surfactants, sorbitol esters e.g. sorbitan fatty acid esters (sorbitan monooleate, sorbitan tristearate), poly(ethylene glycol)-sorbitan fatty acid esters, alkylpolyglycosides, N-alkylgluconamides; alkyl methyl sulfoxides; alkyldimethylphosphine oxides e.g. tetradecyldimethylphosphine oxide;

Zwitterionic Surfactants:
Sulfobetaines; carboxybetaines; alkyldimethylamine oxides e.g. tetradecyldimethylamine oxide;

Polymeric Surfactants:
Di-, tri- and multi-block copolymers of the type $(AB)_x$, ABA and BAB: e.g. poly(ethylene oxide)-poly(propylene oxide) block copolymer, polystyrene-poly(ethylene oxide) block copolymer;
AB-comb copolymers e.g. polymethacrylate-poly(ethylene oxide) comb copolymer;

and Further Other Surfactants:
such as e.g. perfluorosurfactants; silicone surfactants; phospholipids e.g. lecithin or chemically modified lecithins; amino acid surfactants e.g. N-lauroylglutamate; surface-active homopolymers and copolymers e.g. polyvinylpyrrolidone, polyacrylic acid, poly(vinyl alcohol), poly(ethylene oxide), maleic anhydride-isobutene copolymers, vinylpyrrolidone-(vinyl acetate) copolymers;

In these cases the alkyl chains of the above-mentioned auxiliary agents can be linear or branched.

The lengths of the alkyl chains are generally in the range $8<n<20$.

The compositions of the invention comprising compounds of the formula I and 0 to 60 wt. % of other active ingredients and/or surfactants and/or other performance materials.

Preference is given to the novel solid formulations, which comprise the novel plant growth regulator composition comprising compounds of the formula I. They comprise 5 to 100 wt. % of compounds of the formula I, especially of compounds of the formula II.

Preference is also given to the novel suspension concentrates. The comprise a composition comprising a compound I and a thickening agent as abovementioned. It is possible to add other active ingredients, especially in the range of from 0 to 50 wt. %, preferably in the range of 0 to 30 wt. %, surfactants and/or performance materials. These suspension concentrates comprise compounds of the formula I in the range of from 30 to 90 wt. %, especially of from 50 to 80 wt. %, and thickening agents in the range of from 0 to 1 wt. %. Preferably thickening agents like xanthane, e.g. Kelzan S (Kelco/Monsanto Performance Materials Company), especially in the range of 0 to 1 wt. % are used.

Furthermore another aspect of this invention is directed to compositions comprising mepiquat monoborate salts of the formula IV, which are used as PGRs.

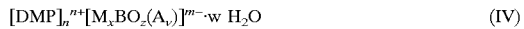
$$[DMP]_n{}^{n+}[M_xBO_z(A_v)]^{m-}\cdot w\ H_2O \qquad (IV)$$

wherein:

DMP is N,N-dimethylpiperidinium (mepiquat);

M is a cation of an agrivulturally acceptable metal, hydrogen or $NH_4$;

B is boron;

O is oxygen,

A is a chelate or complex-forming moiety associated with at least one boron atom;

n and m are the same integer in the range of from 1 to 6;

x is an integer or fraction in the range of from 0 to 10;

z is an integer or fraction in the range of from 0 to 48;

v is an integer or fraction in the range of from 0 to 24; and w is an integer or fraction in the range of from 0 to 24.

The parts of water in formula IV represent free or coordinated inner crystalline water or "bonded" water, which is typically expressed as condensed water of boron-bounded hydroxy groups for structures of borate.

These compositions can be used as plant growth regulators. The abovementioned facts like application rates, treated plants and so on are applicable.

Concerning the formulation of these compositions the above-mentioned adjuvants, parameters and the like are also applicable.

The following examples are intended to illustrate desirable formulations and plant growth improvements provided according to the invention. However, as will be apparent, they are not intended as limitations thereon.

EXAMPLE 1

Preparation of N,N-dimethylpiperidinium Hydroxide Solutions Via Dipolar Electrodialysis The electrochemical process of this Example was carried out by the general method described by H. Stratmann et al., Chemtech (6) (1993) 17–24.

A bipolar electrodialysis cell is constructed by alternating from five bipolar membranes, (commercially available as "Neosepta BP1" from Tokuyama Corp., Japan), with five anion exchange membranes, (commercially available as "AMH" membranes, from Tokuyama Corp., Japan), each having dimensions of 13 cm by 6 cm. The total active membrane area is about 3.78 $dm^2$. The membrane spacing is 0.5 mm. The base compartments are charged with 1000 g of a 10 wt. % strength aqueous solution of N,N-dimethylpiperidinium chloride. The acid compartments are charged with 1000 g of 0.5 wt. % strength hydrochloric acid. After the electrodialysis current (3.78A) has been turned on, the two liquids are recirculated at a flow rate of about 20 l/h at 40° C.

After an electrodialysis time of 240 min the initial chloride concentration in the base compartments (2.37 wt. %) has been reduced to less than 0.1 wt. %, which means that the Cl-depletion achieved is 99.5%. The result is 923 g of a 9.1 wt. % strength N,N-dimethylpiperidinium hydroxide solution as the output from the base compartments and 994 g of about 3 wt. % strength hydrochloric acid as the output from the acid compartments.

EXAMPLE 2

Electrochemical Preparation of N,N-dimethylpiperidinium Hydroxide with Oxidation of Chloride to Elemental Chlorine as the Anode Reaction The electrochemical process of this Example was carried out by the general method described in GB-A 1066930 (Monsanto). A conventional plate/frame electrolytic cell is converted into a bipartite cell by a cation exchange membrane (commercially available as Nafion® 430 from Du Pont) which is fitted between the anode and the cathode. The active anode area and cathode area are a $dm^2$ each. The anode is a DSA, and the cathode is an alloy steel (RA4) electrode.

The catholyte is present in the form of 1000 g of an aqueous 0.5 wt. % strength N,N-dimethylpiperidinium hydroxide solution. The anolyte consists of 1000 g of an aqueous 30 wt. % strength N,N-dimethylpiperidinium chloride solution. At 40° C. and 10A, the transfer of N,N-dimethylpiperidinium cations from the anolyte circuit into the catholyte circuit takes place at cell voltages of 6–10 V. At the same time chlorine is generated at the anode.

After 8 h the catholyte output obtained consists of 1370.7 g of an aqueous 15.6 wt. % strength N,N-dimethylpiperidinium hydroxide solution. The solution has a residual chlorine content of 140 ppm. Based on the conversion ratio observed of 71.3%, the overall current yield is 54.7%.

EXAMPLE 3

Preparation of N,N-dimethylpiperidinium $[B_5O_6(OH)_4]$-solution by Bipolar Electrodialysis—Compound 1.0

The bipolar electrodialysis cell consists of an alternating arrangement of five bipolar membranes (e.g. (Aqualytics, polysulfone type) and five anion exchange membranes (e.g. AM-3, Tokuyama Corp.) having a total membrane area of 10 $dm^2$ and a membrane spacing of 0.5 mm. Integrated in the base loop is a receiving vessel with a stirring unit into which 13.3 kg of boric acid is precharged before the start of the electrolysis. A solution of 50.0 kg of a 12 wt. % solution of mepiquat chloride is put into the base circuit. In the acid loop a 0.5 wt. % solution of sodium chloride is made ready which during the electrodialysis is kept within a pH range of between 6 and 8 by metering in 29.0 kg of a 10 wt. % solution of sodium hydroxide. Circulating in the electrode circuit is a 5 wt. % solution of sodium sulfate. The anode and cathode are made of platinum. After 48 h at 40° C., a flow rate of 100 l/h and an initial current density of 5.7 A/$dm^2$ the chloride ion concentration has decreased from 2.86 wt. % to 0.12 wt. %, corresponding to a degree of desalination of 96.2%. The boric acid in the receiving vessel is completely dissolved in the course of the electrolysis. The base loop contains 59.2 kg of a 22.7 wt. % solution of $DMP^+[B_5O_6(OH)_4]^-$. The yield with reference to DMP amounts to 99.5% and the current efficiency is 93.2%.

EXAMPLE 4

Example 4a

Synthesis of a Mixture of N,N-dimethylpiperidinium Dicarbonate and N,N-dimethylpiperidiniumcarbonate (mepiquat bicarbonate and mepiquat carbonate)

A mixture of 68,1 g of N-methylpiperidine (purity 80%, containing 20% water) [0,551 mol of N-methylpiperidine, 0.756 mol of water], 99.3 g of dimethyl carbonate [1.103 mol] and 88.3 g of methanol [2.759 mol] was pumped at a temperature of 160° C. and a pressure of 60 bar at the rate of 100 ml/h through a 50 ml tubular flow reactor [d;=4 mm, 1=4 m, wall thickness 1 mm, stainless-steel].

Then the reaction mixture was transferred into a distillation flask with a 20 cm Vigreux column and a manually controlled column head and subjected to distillation at normal pressure. The low-boiling fractions distilling off were replaced by continuous addition of water [340 g]. During the distillation process the temperature to the distillation flask was between 72 and 102° C. at the bottom, temperatures of 67 to 99° were measured at the head of the column.

Ion chromatographic analysis of the distillation residue [313 g] resulted in a mepiquat cation content of 19.5 m% [97.2% of theory]. By means of titration, 3.3 g of $CO_3^{2-}$ at the bottom/100 g and 4.1 g of $HCO_3^-$/100 g were measured as anion [100% of theory]. Head-space GC analysis yielded a methanol content of 50 ppm and a dimethyl carbonate content of <100 ppm.

Example 4b

Synthesis of N,N-dimethylpiperidiniumbicarbonate

Carbon dioxide was passed for 1 hour into 553 g of a 15.56% strength aqueous N,N-dimethylpiperidinium hydroxide solution. The solution heated up from 20° C. to 38° C. within °minutes, and then cooled down again. 300 ml of toluene was added to 100 ml of the solution. The resultant mixture was refluxed and the water was distilled off azeotropically over a period of 11 hours.

The precipitated solid was suction filtered, washed with pentane and dried at 50° C. under reduced pressure. 14,2 g of a white, extremely hygroscopic product was obtained.

$^1$H NMR ($D_2O$; δ[ppm]): δ=1.65 (2H); 1.88 (4H); 3.10 (6H); 3.34 (4H). $^{13}$C NMR (($D_2O$; δ[ppm]): δ=22.4; 23.0; 53.9; 162.0 ($HCO_3^-$).

Example 5

N,N-Dimethylpiperidinium Sodium Decaborate Hexahydrate ([N,N-di-methylpiperidinium]$^+$ $[B_{10}NaO_{16}]^-$×7 $H_2O$)—Compound No. 1.1

During stirring 22.4 g (362 mmol) of boric acid (99.8% purity), 24.2 g (35.8 mmol) of N,N-dimethylpiperidinium hydroxide as a 19.6 wt. % aqueous solution, and 2.87 g of sodium hydroxide as a 50 wt. % aqueous solution (35.9 mmol) were added to 150 ml of distilled water. The mixture turned into a clear solution after stirring for about 1 hour. After the water had been removed by evaporation under vacuum, the solid residue was dried another two days under vacuum at 40° C.

The crude material was analyzed in order to confirm the proposed molecular composition and formula. The material contained 6 parts of water as structurally boron-bonded hydrate (typically via hydroxy groups) or crystalline hydrates (free water groups); (See, e.g., Hollemann-Wiberg, "Lehrbuch der Anorg. Chemie", 81.-90. Aufl., page 631 ff.)

RESULTS

1) Elementary analysis in % for C, H, and N:
   calculated: 13.4, 4.8, 2.2, respectively
   found: 13.5, 4.6, 2.1, respectively
2) FID anylsis in % for B and Na:
   calculated: 17.2, 3.7, respectively
   found: 17.8, 3.5, respectively
3) Analysis of [N,N-dimethylpiperidinium]$^+$ cation:
   calculated: 18.7%, respectively
   found: 17.97%, respectively
4) Hygroscopicity of compound 1.1 in comparison to mepiquat chloride:
   Both compounds were dried to a constant dry weight in vacuum at 40° C. 48 hours. Afterwards approx. 1 g samples (two series of 3 samples each and average values) were stored under 50 and 60% relative humidity in air for 2 and/or 4 weeks. The following results in relative water uptake (wt. % w/w) were found:

|  | 50% | | 60% | |
|---|---|---|---|---|
| Relative Humidity | 2 weeks | 4 weeks | 2 weeks | 4 weeks |
| mepiquat chloride | 52 | 58 | 71 | 78 |
| compound 1.1 | 4.1 | * | 7.8 | * |

* not measured 5) pH in water 1 wt. % concentration 6.78
6) Crystallization and recrystallization trials
   As described before, rapid removal of water under vacuum leads to the amorphous compound No. 1.1 according to the proposed formula, while a slow crystallization process under ambient pressure and slow self evaporation of water of the crude concentrate of the reaction product leads to large crystals, which were analyzed by x ray.

Under slow and successive crystallization and recrystallization conditions a 1:1 mixture of relatively large crystals of sodium pentaborate and mepiquat pentaborate is obtained.

A) Sodium pentaborate: $B_{10}Na_2O_{16} \times 10\ H_2O$—Compound 1.1a (ref. CAS reg. Number 12007-92-0, synonym $B_5NaO_8 \times 5\ H_2O$)

The structure was confirmed by x ray analysis and is characterized by the following crystal data:
   Formula weight: 590.24;
   Crystal system: monoclinic;
   Space group C2/2;
   Unit cell dimensions: a=1105.71 (11) pm; alpha=90°;
   b=1638.5 (2) pm; beta=112.757 (8)°;
   c=1355.13 (9) pm; gamma=90°;
   volume, z: 2.2640 (3) nm$^3$;
   density (calc.) 1.732 Mg/m$^3$;

B) N,N-Dimethylpiperidinium pentaborate dihydrate—Compound 1.1b ([N,N-Dimethylpiperidinium]$^+$[$B_5O_8$]$^- \times 2\ H_2O$)

The structure was confirmed by x ray analysis. The structure shows the same anionic pentaborate spiro type like sodium pentaborate; Selected crystals were dried under vacuum at 150° C. for two days and were characterized by the following crystal data:
   Formula weight: 332.29;
   Crystal system: triclinic;
   Space group: P1;
   Unit cell dimensions: a=932.6 (2) pm; alpha=96.063 (11);
   b=938.57 (14) pm; beta=102.48 (2)°;
   c=1846.7 (4) pm; gamma=96.50 (2)°;
   volume z: 1.5540 (5) nm$^3$;
   density (calc.): 1.420 Mg/m$^3$.

EXAMPLE 6

[Dimethylpiperidinium]$_2^{2+}$[$B_{18}Na_2O_{29}$]$^{2-} \times 8\ H_2O$—Compound 1.2

The above compound was prepared in the same manner as compound 1.1 using the following starting materials in the relative molar quantities as stated: 1 part dimethylpiperidinium hydroxide, 9 parts boric acid (commercially available from Merck Company Darmstadt (Germany) 99.8% purity, CAS Reg. Number 10043-35-3) and 1 part sodium hydroxide. The compound was analyzed in the same manner as compound 1.1 in Example 5 by elementary analysis with the following results:

1) Analysis in % for C, H, N, B, Na and Cl:
   calculated: 16.6, 4.5, 2.6, 18.1, 4.3, 0.0, respectively
   found: 15.8, 4.7, 2.6, 17.8, 3.9, 0.088, respectively
2) Appearance:
   glassy solid
3) Hygroscopicity:
   4 weeks at 50% relative humidity in air: 5.2 wt. % water uptake
   4 weeks at 60% relative humidity in air: 7.0 wt. % water uptake
4) pH in water 1 wt. % concentration: 7.4

EXAMPLE 7

[Dimethylpiperidinium]$_2^{2+}$[$B_{12}Na_4O_{21}$]$^{2-} \times 20\ H_2O$—Compound 1.3

The above compound was prepared in the same manner as compound 1.1 using the following starting materials in the relative molar quantities as stated: 1 part dimethylpiperidinium hydroxide; 2 parts boric acid; and 1 part borax (commercially available from Riedel de Haen Company; 99.5% pur.; CAS Reg. Number 1303-96-4 $Na_2B_4O_7 \times 10\ H_2O$). The compound was analyzed in the same manner as compound 1.1 in Example 5 with the following results:

1) Analysis in % for C, H, N, B, Na and Cl:
   calculated: 14.7, 6.3, 2.4, 11.3, 8, 0.0, respectively
   found: 14.6, 6.4, 2.6, 11.6, 8, 0.013, respectively
2) Appearance:
   crystalline
3) Hygroscopicity
   4 weeks at 50% relative humidity in air: 13.6 wt. % water uptake
   4 weeks at 60% relative humidity in air: 28.8 wt. % water uptake

EXAMPLE 8

[Dimethylpiperidinium]$^+$[B$_9$C$_{27.6}$H$_{50.6}$Na$_{0.8}$O$_{39.7}$]$^-$×8 H$_2$O—Compound 1.4

The above compound was prepared in the same manner as compound 1.1 using the following starting materials in the relative molar quantities as stated: 1 part dimethylpiperidinium hydroxid, 9 parts boric acid; 2.3 parts saccharose; 0.8 parts sodium hydroxide. (It is to be noted non-stoichiometric molar parts of starting materials, esp. of sodium hydroxide, were used, in order to get pH values of the resulting formulations of about 7; this leads as well to the non-stoichiometric formula shown above.) The compound was analyzed in the same manner as compound 1.1 in Example 5 with the following results:

1) Analysis in % for C, H, N, B, Na and Cl:
   calculated: 29.8, 5.9, 1, 7, 1.3, 0.0, respectively
   found: 29.2, 5.9, 0.9, 7, 1.3, 0.031, respectively
2) Appearance:
   crystalline
3) Hygroscopicity:
   not measured

EXAMPLE 9

[Dimethylpiperidinium]$^+$[B$_8$(NH$_4$)$_{0.3}$O$_{12.7}$]$^-$×4 H$_2$O (proposed formula according analysis)—Compound 1.5

The above compound was prepared in the same manner as compound 1.1 using the following starting materials in the relative molar quantities as stated: 1 part dimethylpiperidinium hydroxide, 8 parts boric acid, 0.3 parts ammonium hydroxide. (As in Example 6, non-stoichiometric molar parts of starting materials, especially of ammonium hydroxide, were used, in order to get pH values of the resulting formulations of about 7; this leads as well to the non-stoichiometric formula shown above.) The compound was analyzed in the same manner as compound 1.1 in Example 5 with the following results:

1) Analysis in % for C, H, N, B, Na and Cl:
   calculated: 17.4, 5.5, 6.7, 18.0, 0.0, 0.0, respectively
   found: 17.3, 5.6, 4.2, 17.6, 0.01, 0.015, respectively
2) Appearance:
   crystalline
3) Hygroscopicity:
   4 weeks at 50% relative humidity in air: 0.4 wt. % water uptake
   4 weeks at 60% relative humidity in air: 0.6 wt. % water uptake
4) pH in water 1 wt. % concentration:
   6.8

EXAMPLE 10

[Dimethylpiperidinium]$^+$[B$_9$Na$_{0.9}$O$_{14.5}$]$^-$×6 H$_2$O—Compound 1.6

The above compound was prepared in the same manner as compound 1.1 using the following starting materials in the relative molar quantities as stated: 1 part dimethylpiperidinium hydroxide; 9 parts boric acid; 0.9 parts sodium hydroxide. (As in Example 6, non-stoichiometric molar parts of starting materials, especially of sodium hydroxide, were used, in order to get pH values of the resulting formulations of about 7; this leads as well to the non-stoichiometric formula shown above.) The compound was analyzed in the same manner as compound 1.1 in Example 5 with the following results:

1) Analysis in % for C, H, N, B, Na and Cl:
   calculated: 14.7, 4.9, 21.4, 17.0, 3.6, 0.0, respectively
   found: 14.4, 4.7, 21.4, 17.6, 3.9, 0.099, respectively
2) Appearance:
   amorphous
3) Hygroscopicity:
   4 weeks at 50% relative humidity in air: 2.7 wt. % water uptake
   4 weeks at 60% relative humidity in air: 9.0 wt. % water uptake
4) pH in water 1 wt. % concentration:
   7.1

EXAMPLE 11

[Dimethylpiperidinium]$^+$[B$_{6.4}$Na$_{0.3}$O$_{10.3}$]$^-$×4 H$_2$O—Compound 1.7

The above compound was prepared in the same manner as compound 1.1 using the following starting materials in the relative molar quantities as stated: 1 part dimethylpiperidinium hydroxide; 6.4 parts boric acid; 0.3 parts sodium hydroxide. (As in Example 6, non-stoichiometric molar parts of starting materials, especially of sodium hydroxide, were used, in order to get pH values of the resulting formulations of about 7; this leads as well to the non-stoichiometric formula shown above.) The compound was analyzed in the same manner as compound 1.1 in Example 5 with the following results:

1) Analysis in % for C, H, N, B, Na and Cl:
   calculated: 19.7, 5.6, 3.3, 16.2, 1.6, 0.0, respectively
   found: 19.7, 5.4, 3.3, 16.5, 1.6, 0.046, respectively
2) Appearance:
   amorphous
3) Hygroscopicity:
   4 weeks at 50% relative humidity in air: 1.9 wt. % water uptake
   4 weeks at 60% relative humidity in air: 4.1 wt. % water uptake

EXAMPLE 12

[Dimethylpiperidinium]$^+$[B$_9$C$_9$H$_{36}$Na$_{0.8}$O$_{23.4}$]$^-$×5 H$_2$O—Compound 1.8

The above compound was prepared in the same manner as compound 1.1 using the following starting materials in the relative molar quantities as stated: 1 part dimethylpiperidinium hydroxide; 9 parts boric acid; 0.8 parts sodium hydroxide; 4.5 parts ethylene glycol. (As in Example 6, non-stoichiometric molar parts of starting materials, especially of sodium hydroxide, were used, in order to get pH values of the resulting formulations of about 7; this leads as well to the non-stoichiometric formula shown above.) The compound was analyzed in the same manner as compound 1.1 in Example 5 with the following results:

1) Analysis in % for C, H, N, B, Na and Cl:
   calculated: 22.9, 7.4, 1.7, 11.6, 2.2, 0.0, respectively found: 23.2, 6.3, 1.7, 11.7, 1.9, 0.046, respectively
2) Appearance:
   glassy
3) Hygroscopicity:
   not measured
4) pH in water 1 wt. % concentration:
   not measured

EXAMPLE 13

N,N-Dimethylpiperidinium pentaborate dihydrate semihydrate ([N,N-Dimethylpiperidinium]$^+$ [B$_5$O$_6$]$^-$×2.5 H$_2$O)—Compound 1.9

The above compound was prepared in the same manner as compound 1.1 using the following starting materials in the relative molar quantities as stated: 1 part dimethylpiperidinium hydroxide; 5 parts boric acid; For analysis a sample of crude material was crystallized at room temperatur by self evaporation of water. The resulting crystals were isolated by filtration and dried at room temperature.

The structure of the compound was confirmed by x ray analysis. It is identical with compound 1.1b but one additional water molecule is incorporated by two crystal units; this leads to the following overall formula: [N,N-Dimethylpiperidinium]$^+$[B$_5$O$_6$]$^-$×2.5 H$_2$O;

1) Appearance:
   crystalline, mp.: >400° C.; significant mass reduction >10% at >200° C. due to condensation processes of the pentaborate anion;
2) Hygroscopicity:
   4 weeks at 50% relative humidity in air: 0.4 wt. % water uptake
   4 weeks at 60% relative humidity in air: 0.6 wt. % water uptake

EXAMPLE 14 (Corrosion trials)

Comparison of (A) mepiquat chloride, with (B) a mixture of mepiquat chloride with disodium octaborate tetrahydrate (Solubor®), and (C) mepiquat pentaborate (compound 1.9) of example 13.

The tests of this example were conducted according to the method of DIN (Deutsche Industrie Norm) No. 52168, part 1 of November 1981, but using modified steel plates.

The corrosion tests were conducted on the three different formulations prepared as set forth below. Each formulation was tested with the different steel types set forth below.

The first formulation, referred to as "mepiquat chloride" in the tables below, was an 8.33% mepiquat chloride aqueous solution (by weight) prepared by diluting a 600 g/l mepiquat chloride preconcentrate. The second formulation, referred to as "mepiquat chloride plus borate salt" in the tables below, was prepared by adding 15 wt. % disodium octaborate tetrahydrate to the same 8.33% aqueous solution of mepiquat chloride as was used in the first formulation.

The third formulation, referred to as "mepiquat pentaborate"—in the tables below, was prepared from compound 1.9, example 13 by diluting with water to form a 12% mepiquat pentaborate (wt. %) aqueous solution.

All three abovementioned formulations contained equal amounts of the mepiquat cation.

One-half liter quantities of each formulation were placed in polyethylene plastic containers (10 cm×10 cm×12 cm (height)). Into each of the containers, two series of steel plate types—12×5 cm$^2$ (0.2 cm thickness) were inserted.

In modification of the mentioned DIN, the steel plates were prepared with an additional oxyacetylene torched area, approximately 5to 7 mm large, horizontally in the middle of the steel plates.

The torched areas were placed below the solution's surface.

(The aim of this modification of the test was to simulate a more erious corrosion and endangering situation.)

the position of the plates were such that approximately ⅓ of the plates were in air contact. After 14 days the steel plates were examined, washed and cleaned, dried and weighed according to the DIN method above.

Results: From the corrosion results set forth below, (particularly based on loss of material in g/m$^2$) it can be seen that the "mepiquat pentaborate" is a non-corrosive material (test series 1 and 2).

| Formulation | Test series 1: Steel Type ST 37 | | | | |
| --- | --- | --- | --- | --- | --- |
| | Starting weight in g | End weight in g | difference in g | corrosion g/m$^2$ | pH values initial . . . end |
| mepiquat chloride[1] | 95,2394 | 94,9213 | 0,3181 | 35,34 | 7.67 . . . 7.96 |
| mepiquat chloride plus borate salt[2] | 95,3464 | 95,1032 | 0,2432 | 27,02 | 7.33 . . . 7.55 |
| mepiquat pentaborate[3] | 96,7572 | 96,7424 | 0,0148 | 1,64 | 7.40 . . . 7.43 | notes about the appearance of the resulting formulations:
[1]yellow to orange solution, cloudy, sedimentations
[2]similar to [1]
[3]clear solution, almost colorless, no sedimentation

| Formulation | Test series 2: Steel Type ST 13 | | | | |
| --- | --- | --- | --- | --- | --- |
| | Starting weight in g | End weight in g | difference in g | corrosion g/m$^2$ | pH values initial . . . end |
| mepiquat chloride[1] | 92,4708 | 92,2512 | 0,2196 | 24,4 | 7.67 . . . 8.34 |
| mepiquat chloride plus borate salt[2] | 92,0985 | 91,9047 | 0,1938 | 21,53 | 7.33 . . . 7.46 |
| mepiquat pentaborate[3] | 93,2139 | 93,2132 | 0,0007 | <0.1 | 7.40 . . . 7.43 | notes about the appearance of the resulting formulations:
[1]yellow to orange solution, cloudy, sedimentations
[2]similar to [1]
[3]clear solution, colorless, no sedimentation

Example 15 (formulation)

The following three recipes describe novel suspension concentrates with boric acid, borax and mepiquat pentaborate as starting materials. The formulations include here a ratio of >1:30 of mepiquat and boron. In all formulations the amount of the mepiquat cation is 32 g/l.

Example 15a

To 232.9 g of a 15.8 wt. % aqueous solution of mepiquat hydroxide (0.28 mol) a mixture of 182 g of boric acid (2.94 mol) and 561.4 g of borax ($Na_2B_4O_7 \times 10\ H_2O$, 1.47 mol) was added with stirring with a lab dispenser. After 10 min 16.6 g of a pre-concentrate of Kelsan S* (2% in water) and 288.8 g of destined water were added.

* Kelzan S is a xanthan gum product of the Kelco/Monsanto Performance Materials Company and used as thickening agent The mixture was stirred for about 1 hour. The resulting suspension concentrate was stable, colorless, homogenous and could be used as ready mix in tankmix applications under full dissolution of all components.

The ratio of 1:32 of mepiquat to boron was confirmed by ion chromatography and elementary analysis.

Example 15b

The following suspension concentrate was prepared in the same manner as example 15a using the following starting materials in the quantities as stated: 232.9 g of a 15.8 wt. % aqueous solution of mepiquat hydroxide (0.28 mol), 544.1 g of boric acid (8.80 mol), 76.64 g of Solubor® (0.23 mol), 16.6 g of Kelsan S* (as 2 wt. % preconcentrate in water) and 323.05 g of destined water.

The ratio of 1:38 of mepiquat to boron was confirmed by ion chromatography and elementary analysis.

Example 15c

The following suspension concentrate was prepared in the same manner as example 15a using the following starting materials in the quantities as stated: 98.35 g of mepiquat pentaborate (0.28 mol) of example 13, 383.2 g of Solubor ($Na_2B_8O_{13} \times 4\ H_2O$) (CAS reg. no. 12608-41-2) (1.14 mol), 16.6 g of Kelsan S* (as 2% preconcentrate in water) and 704 g of destined water.

The ratio of 1:32.5 of mepiquat to boron was confirmed by ion chromatography and elementary analysis.

EXAMPLE 16

Biological Tests

There is no reduction of biological activity of the new borate compositions of mepiquat as compared to mepiquat chloride. As can be seen from the following tables, certain borate compositions are even more active in terms of reducing shoot elongation in cotton plants.

The following formulations D to J were used in the experiments a to e. Formulation H including only mepiquat chloride was used as standard.

Formulation J is a solution of the dissolved compound 1.1b or 1.9 in water and formulation F is a solution of the compound of the composition 1.2.

| | Formulation Recipes (g/l) | | | | | | |
|---|---|---|---|---|---|---|---|
| | D | E | F | G | H | I[1] | J[1] |
| mepiquat chloride (used as 627.8 g/l concentrate) | — | — | — | — | 42.2 | — | — |
| mepiquat hydroxide 18.67 wt % (in water) | 197.08 | 197.08 | 197.08 | 197.08 | — | 394.2 | 393.9 |
| boric acid | 121.8 | 34.8 | 174 | 17.4 | — | 139.3 | 173.9 |
| borax | 53.84 | — | — | — | — | — | — |
| solubor ® | — | 156.4 | — | — | — | — | — |
| citric acid (0.33 mol) | — | — | — | 19.68 | — | — | — |
| sodium hydroxide - 50 wt. % (in water) | — | — | 44.96 | — | — | — | — |
| destilled water ad. 1000 ml | 688 | 696 | 685 | 772 | 958 | 523 | 489 |
| analysis and other parameters: | | | | | | | |
| mepiquat cation (found) | 32.6 | 30.5 | 33.4 | 31.2 | 32 | 62.8 | 64 |
| mepiquat cation (calc.) | 32 | 32 | 32 | 32 | 32 | 32 | 64 |
| mols of boron per liter | 2.53 | 2.81 | 2.53 | 0.28 | — | 4.49 | 2.81 |
| ratio (molar parts) of mepiquat:boron:sodium | 1:9:1 | 1:10:2 | 1:9:1 | 1:1:0 | | 1:4:0 | 1:5:0 |
| densities: g/ml | 1.071 | 1.084 | 1.100 | 1.006 | 1.000 | 1.056 | 1.057 |

[1]Double concentration of the mepiquat cation were used here.

EXPERIMENT A

Shoot length reduction in wheat (cv. "Ralle") by different borate formulations of mepiquat as compared with mepiquat chloride.*

* Cultivation of plants under green house conditions. Spray application with 750 l/ha of aqueous solution at a shoot length of 16 cm. Evaluations were made 20 days after treatment at a shoot length of 55 cm of the control plants.

| Preparation | Rate of mepiquat [g cation/ha] | Shoot length [% of control] |
|---|---|---|
| Mepiquat chloride = | | |
| H | 500 | 74 |
| | 1000 | 67 |
| | 1500 | 69 |
| | 2000 | 66 |
| D | 500 | 83 |
| | 1000 | 76 |
| | 1500 | 76 |
| | 2000 | 74 |
| E | 500 | 76 |
| | 1000 | 80 |
| | 1500 | 73 |
| | 2000 | 73 |
| F | 500 | 77 |
| | 1000 | 73 |
| | 1500 | 74 |
| | 2000 | 72 |

-continued

| Preparation | Rate of mepiquat [g cation/ha] | Shoot length [% of control] |
|---|---|---|
| G | 500 | 76 |
|  | 1000 | 72 |
|  | 1500 | 68 |
|  | 2000 | 64 |
| J | 1000 | 70 |
|  | 2000 | 63 |

EXPERIMENT B

Shoot length reduction in cotton (cv. "Delta Pine") by different borate formulations of mepiquat as compared with mepiquat chloride [mepiquat rate=250 g cation/ha]*.

* Cultivation of plants under greenhouse conditions. Spray application with 400 l/ha of aqueous solution at a shoot length of 23 cm. Evaluations were made 27 days after treatment at a shoot length of 53 cm of the control plants.

| Preparation | Shoot length [% of control] |
|---|---|
| Mepiquat chloride = |  |
| H | 58 |
| D | 63 |
| E | 56 |
| F | 55 |
| G | 58 |

EXPERIMENT C

Shoot length reduction in cotton (cv. "Delta Pine") by different borate formulations of mepiquat as compared with mepiquat chloride*

| Preparation | Rate of mepiquat [g cation/ha] | Shoot length [% of control] |
|---|---|---|
| Mepiquat chloride = |  |  |
| H | 25 | 79 |
|  | 50 | 74 |
|  | 100 | 77 |
|  | 200 | 81 |
| D | 25 | 74 |
|  | 50 | 74 |
|  | 100 | 77 |
|  | 200 | 68 |
| E | 25 | 77 |
|  | 50 | 79 |
|  | 100 | 75 |
|  | 200 | 69 |
| F | 25 | 80 |
|  | 50 | 73 |
|  | 100 | 72 |
|  | 200 | 68 |
| G | 25 | 83 |
|  | 50 | 80 |
|  | 100 | 74 |
|  | 200 | 60 |
| I | 50 | 75 |
|  | 100 | 71 |
|  | 200 | 73 |

* Cultivation of plants under greenhouse conditions. Spray application with 400 l/ha of aqueous solution at a shoot length of 25 cm. Evaluations were made 20 days after treatment at a shoot length of 37 cm of the control plants.

EXPERIMENT D

Shoot length reduction in cotton (cv. "Delta Pine") by different borate formulations of mepiquat as compared with mepiquat chloride*

* Cultivation of plants under greenhouse conditions. Spray application with 400 l/ha of aqueous solution at a shoot length of 25 cm. Evaluations were made 21 days after treatment at a shoot length of 40 cm of the control plants.

| Preparation | Rate of mepiquat [g cation/hal] | Shoot length [% of control] |
|---|---|---|
| Mepiquat chloride = |  |  |
| H | 25 | 85 |
|  | 50 | 84 |
|  | 100 | 76 |
|  | 200 | 76 |
| E | 25 | 84 |
|  | 50 | (68) |
|  | 100 | 75 |
|  | 200 | 77 |
| J | 25 | 91 |
|  | 50 | 80 |
|  | 100 | 73 |
|  | 200 | 76 |

EXPERIMENT E

Shoot length reduction in cotton (cv. "Delta Pine") by different borate formulations of mepiquat as compared with mepiquat chloride.*

* Cultivation of plants under greenhouse conditions. Spray application with 400 l/ha of aqueous solution at a shoot length of 20 cm. Evaluations were made 14 days after treatment at a shoot length of 38 cm of the control plants.

| Preparation | Rate of mepiquat [g cation/ha] | Shoot length [% of control] |
|---|---|---|
| Mepiquat chloride = |  |  |
| H | 25 | 76 |
|  | 50 | 77 |
|  | 100 | 79 |
|  | 200 | 74 |
| E | 25 | 79 |
|  | 50 | 71 |
|  | 100 | 74 |
|  | 200 | 70 |
| J | 25 | 79 |
|  | 50 | 74 |
|  | 100 | 74 |
|  | 200 | 73 |

EXPERIMENT F

Shoot length reduction in cotton (cv. "Delta Pine") by different dorate formulations of mepiquat as compared with mepiquat chloride.*

* Cultivation of plants under greenhouse conditions. Spray application with 400 l/ha of aqueous solution at a shoot length of 30 cm. Evaluations were made 21 days after treatment at a shoot length of 43 cm of the control plants.

| Preparation | Rate of mepiquat [g cation/ha] | Shoot length [% of control] |
| --- | --- | --- |
| Mepiquat chloride = | | |
| H | 25 | 82 |
|  | 50 | 80 |
|  | 100 | 78 |
|  | 200 | 81 |
| Example 15a | 25 | 83 |
|  | 50 | 81 |
|  | 100 | 78 |
|  | 200 | 73 |
| Example 15b | 25 | 80 |
|  | 50 | 75 |
|  | 100 | 76 |
|  | 200 | 77 |
| Example 15c | 25 | 84 |
|  | 50 | 77 |
|  | 100 | 73 |
|  | 200 | 74 |

The invention has been described in considerable detail with reference to its preferred embodiments. However, numerous variations and modifications can be made without departure from the spirit and scope of the invention as described in the foregoing detailed specification and defined in the appended claims.

That which is claimed is:

1. An agriculturally active composition comprising a non-hygroscopic compound having the chemical formula:

$$[DMP]_n^{m+}[M_xB_yO_z(A)_v]^{m-} \cdot w\, H_2O \qquad (I)$$

wherein:
DMP is N,N-dimethylpiperidinium (mepiquat);
M is a cation of an agriculturally acceptable metal, hydrogen, or $NH_4$;
B is boron;
O is oxygen;
A is a chelate or complex-forming moiety associated with at least one boron atom or an agriculturally acceptable cation;
n and m are the same integer in the range of from 1 to 6;
x is an integer or fraction in the range of from 0 to 10;
y is an integer or fraction in the range of from more than 1 to 48;
z is an integer or fraction in the range of from 0 to 48;
v is an integer or fraction in the range of from 0 to 24; and
w is an integer or fraction in the range of from 0 to 24.

2. A composition as claimed in claim 1, wherein x is zero.

3. A composition as claimed in claim 1, wherein x is an integer or fraction in the range of from more than 0 to 10.

4. A composition as claimed in any one of claims 1 to 3, wherein the composition of formula I comprises 2 to 20 molar equivalents of boron per molar equivalent of N,N-dimethylpiperidinium derivative.

5. A composition as claimed in claim 4, wherein the composition of formula I comprises 2 to 10 molar equivalents of boron per molar equivalent of N,N-dimethylpiperidinium derivative.

6. A composition as claimed in claim 5, wherein the composition of formula I comprises 3 to 10 molar equivalents of boron per molar equivalent of N,N-dimethylpiperidinium derivative.

7. The compound as claimed in any one of claims 1 to 3 prepared by reacting 1 to 20 molar equivalents of a suitable boron compound with 1 mole of N,N-dimethylpiperidinium hydroxide, N,N-dimethylpiperidinium carbonate and/or N,N-dimethyl-piperidinium bicarbonate.

8. A process for the preparation of a compound of the formula I as claimed in claim 1, wherein N,N-dimethylpiperidinium hydroxide is reacted with boric acid and/or boron containing oxides and optionally with agriculturally useful metal hydroxides, oxides, carbonates or bicarbonates or ammonium hydroxide, carbonate or bicarbonate and optionally with a chelate or complex-forming moiety A.

9. A process as claimed in claim 8, wherein N,N-dimethyl-piperidinium hydroxide is reacted with boric acid, boron containing oxides and optionally with agriculturally useful metal hydroxides, oxides, carbonates or bicarbonates or ammonium hydroxide, carbonate or bicarbonate.

10. A process for the preparation of a compound of the formula I as claimed in claim 1, wherein N,N-dimethylpiperidinium bicarbonate or carbonate is reacted with boric acid and/or boron-containing oxides and optionally with agriculturally useful metal oxides, hydroxides, carbonates or bicarbonates or ammonium hydroxide, carbonate or bicarbonate and optionally with a chelate or complex-forming moiety A.

11. A process as claimed in claim 10, wherein N,N-dimethylpiperidiuniumbicarbonate or carbonate is reacted with boric acid, boron containing oxides and optionally with agriculturally useful metal hydroxides, oxides, carbonates or bicarbonates or ammonium hydroxide, carbonate or bicarbonate.

12. A composition as claimed in claim 1 comprising a maximum of halide traces or halide contaminations of 1 wt. % (calc. dry).

13. A composition as claimed in claim 1 comprising 0 to 60 wt. % of other active ingredients and/or surfactants and/or other performance materials.

14. A suspension concentrate comprising a composition as claimed in claim 1 and a thickening agent.

15. A suspension concentrate as claimed in claim 14 comprising from 30 to 90 wt. % of a compound of formula I as claimed in claim 1, from 0 to 50 wt. % of another active ingredient, from 0 to 10 wt. % of thickening agent and/or surfactants and/or other performance materials.

16. A suspension concentrate comprising a composition as claimed in claim 2 and a thickening agent.

17. A suspension concentrate comprising from 30 to 90 wt. % of compound of formula I as claimed in claim 1 and from 0 to 10 wt. % of thickening agent.

18. A suspension concentrate as claimed in claim 14 comprising a maximum of halide traces or halide contaminations of 1 wt. % (calc. dry).

19. A method for regulating the plant growth which comprises applying a composition as claimed in claim 1 in solid form or in solution form to a plant.

* * * * *